United States Patent [19]

Macoveanu et al.

[11] 4,104,918
[45] Aug. 8, 1978

[54] ELECTRODYNAMOGRAPH

[75] Inventors: Aurelian Liviu Alexandru Macoveanu; Nicolae Grecu, both of Bucharest, Romania

[73] Assignee: Institutul de Cercetari Stiintifice Pentru Protectia Muncii, Bucharest, Romania

[21] Appl. No.: 710,635

[22] Filed: Aug. 2, 1976

[51] Int. Cl.² ............................................. G01L 5/02
[52] U.S. Cl. ..................................................... 73/379
[58] Field of Search .................... 73/379, 380; 272/67, 272/68

[56] References Cited

U.S. PATENT DOCUMENTS

| | | | |
|---|---|---|---|
| 2,157,790 | 5/1939 | Hutt et al. | 73/380 |
| 2,608,969 | 9/1952 | Gordon | 73/379 |
| 3,420,222 | 1/1969 | Noe et al. | 73/380 |

*Primary Examiner*—Anthony V. Ciarlante
*Attorney, Agent, or Firm*—Karl F. Ross

[57] ABSTRACT

An electrodynamograph for determining, in percentage, the degree of fatigue of the human organism following physical or intellectual effort comprises an actuator which is displaced by the subject and is coupled to a mechanical-electrical transducer producing an output which is applied to a recorder through an electronic switch which provides, by interrupting the recordal, indicia of time. An audio-frequency generator produces a signal which is connected periodically to a loudspeaker through another electronic switch, e.g. a multivibrator-controlled relay, to produce acoustic outputs establishing the cadence or rhythm of operation of the actuator. A trace is produced of the exertion of the individual before and after work and the integrals of the respective traces are determined to establish a percentage representing the fatigue of the subject following the physical or intellectual effort.

3 Claims, 2 Drawing Figures

ELECTRODYNAMOGRAPH

FIELD OF THE INVENTION

The present invention relates to an electrodynamograph and, more particularly, to an apparatus for measuring in percentage the degree of tiredness of the human organism following physical or intellectual effort.

BACKGROUND OF THE INVENTION

There are different types of known dynamometers, dynamographs, ergographs, some of which are mechanical and others of which are mechanical-electrical or mechanical-electronic devices. As a rule, all of these devices operate based on the correlation between the fatigue stage of the organism and its resistance to effort. By initial measurement by a suitable method of the resistance to effort, for instance that of the hand-flexor muscles, before performance of physical or intellectual work, and by a subsequent measurement after completion of the work, one finds that the resistance effort of the muscles diminishes. The diminution of the resistance effort of the respective muscles is especially marked as the overall tiredness, because of the work, of the human organism is greater.

The various dynamometers or dynamographs have various shortcomings that limit their performance and utility.

For example, they cannot establish the effort which serves to provide the measurements with a given rhythm. Since they are incapable of imposing a certain rhythm on the activity of the test subject, the tests are nonreproducible under given conditions, causing arbitrary results upon repetition of the tests with the same subjects and leaving possibly erroneous conclusions. Since it is not possible to impose upon the subject a movement-execution rhythm, the rhythm cannot be varied in spite of the fact that adjustment of the rhythm of the effort makes it possible to choose a rhythm that is the best for each individual subject.

Conventional devices also do not have the capacity to indicate the length of the experimental efforts, although the time factor is extremely important with respect to measurement of the resistance to effort.

Another drawback of known dynamographs is that it is impossible to rigorously check the movements executed by the subject, especially to the extent that it is possible to establish that the tests are reproducible and that a full effort has been exerted at each cycle by the subject.

OBJECTS OF THE INVENTION

It is an object of the present invention, therefore, to provide an improved apparatus for measuring the fatigue of a test subject resulting from physical or intellectual work.

Another object of this invention is to provide an improved method of and apparatus for determining the change in muscular strength or capacity resulting from physical or intellectual work.

SUMMARY OF THE INVENTION

These objects and others which will become apparent hereinafter are attained, in accordance with the present invention, by providing a hand-driven device which comprises a pair of linked levers which are squeezed repeatedly by the subject until he tires. A predetermined rhythm or cadence of squeezing execution is imposed upon the subject by the generation of a sound (acoustic) signal which is periodically interrupted by multivibrator and associated relay and is produced by a loudspeaker. Advantageously, both the cadence (rhythm, frequency) and the level (amplitude) of the acoustic signal are adjustable.

According to the invention, the repeated squeezings of the hand-driven device or actuator are transmitted through a cable to a mobile screen or armature of an inductive transducer which comprises two iron-core coils which are inductively coupled, one of the coils constituting a primary and the other coil constituting a secondary. The output signal of the audio frequency generator is applied to the primary coil so that, in the secondary coil, a current is induced which depends upon the position of the mobile screen or armature and hence the degree to which the handles have been squeezed. This current is shaped, amplified where necessary, filtered and applied to a graphic recorder preferably of the paper-tape-and-pen type on which a curve representing the movements of the subject's hand is obtained as a function of time. The time mark can be produced by interrupting this trace and thereby permitting the pen to swing back to its null or zero position. The electrodynamograph can utilize a multivibrator of adjustable frequency, the output signal of which controls a relay which periodically interrupts the signal applied to the pen recorder. As noted, this causes a periodic return to the pen to its rest position.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
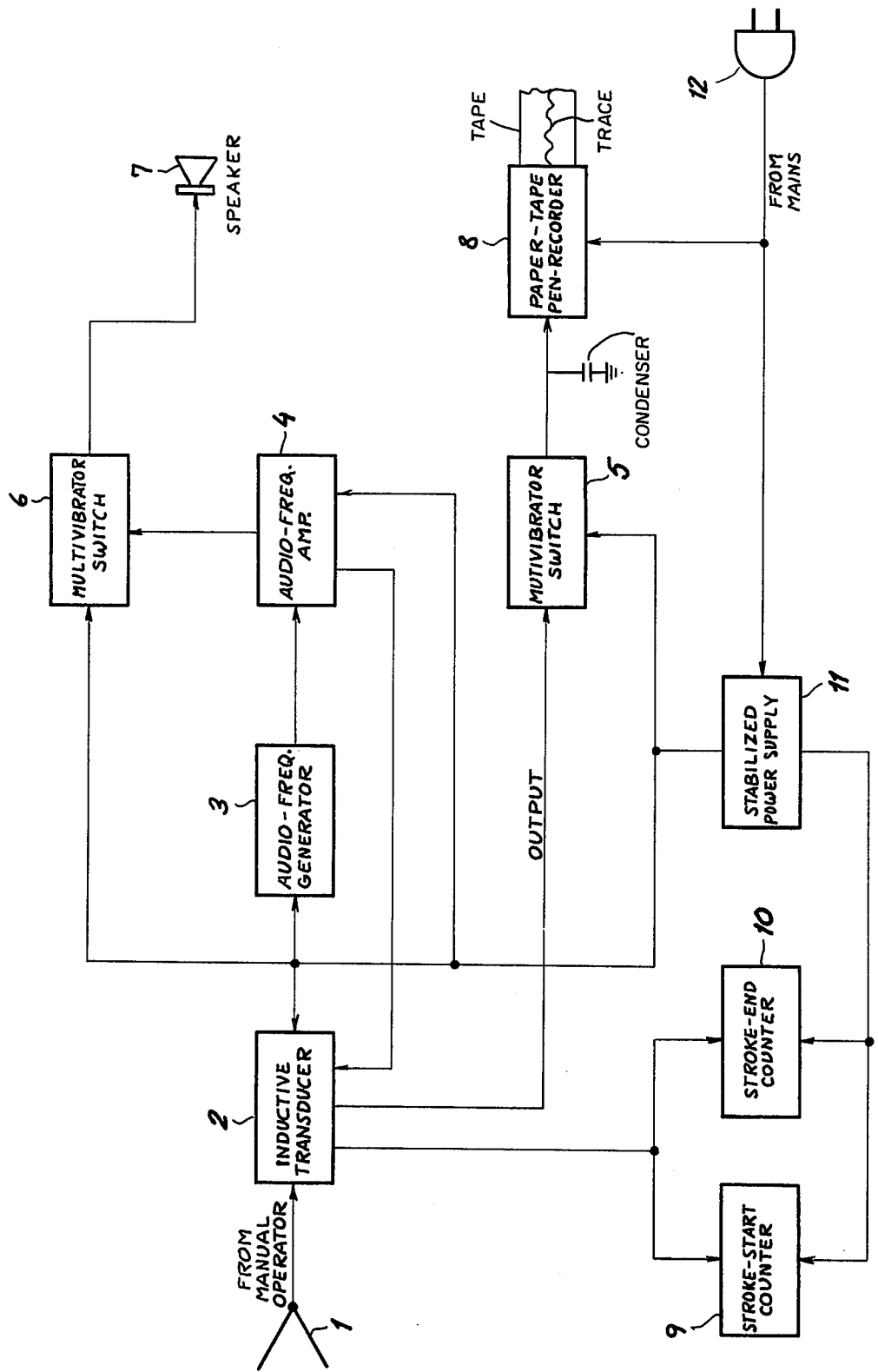
FIG. 1 is a block diagram illustrating the apparatus of the present invention.

From FIG. 1 it will be apparent that the basic elements of the electrodynamograph according to the invention include a hand-driven device 1 comprising a pair of levers which can be squeezed by the subject with a single hand. The mechanical motion of this hand-driven device or actuator is applied to an inductive transducer 2 of the variable-coupling type. The primary winding of this transducer is supplied with an audio frequency alternating current from the audio frequency amplifier 4 and the transducer produces an output which is applied through a multivibrator switch 5 to the paper-tape pen recorder 8.

The apparatus also includes an audio frequency generator 3 which feeds the basic audio frequency signal or tone into the audio frequency amplifier 4 which applies an audio frequency output to a multivibrator switch 6 which, in turn, applies the audio frequency signal to a loudspeaker 7.

The output of the inductive transducer 2 is also applied to a pair of counters 9 and 10, the counter 9 being a stroke-start counter and the counter 10 being a stroke-end counter. A dual-stabilized power supply 11 provides the stabilized electric current input to the counters 9 and 10, to the transducer 2, if necessary, to the audio frequency generator 3, to the multivibrator switch 6, to the audio frequency amplifier 4, and to the multivibrator switch 5. The main current may be supplied by an electric cord 12 to the power supply 11 and to the paper-type pen recorder 8.

Figure 2:
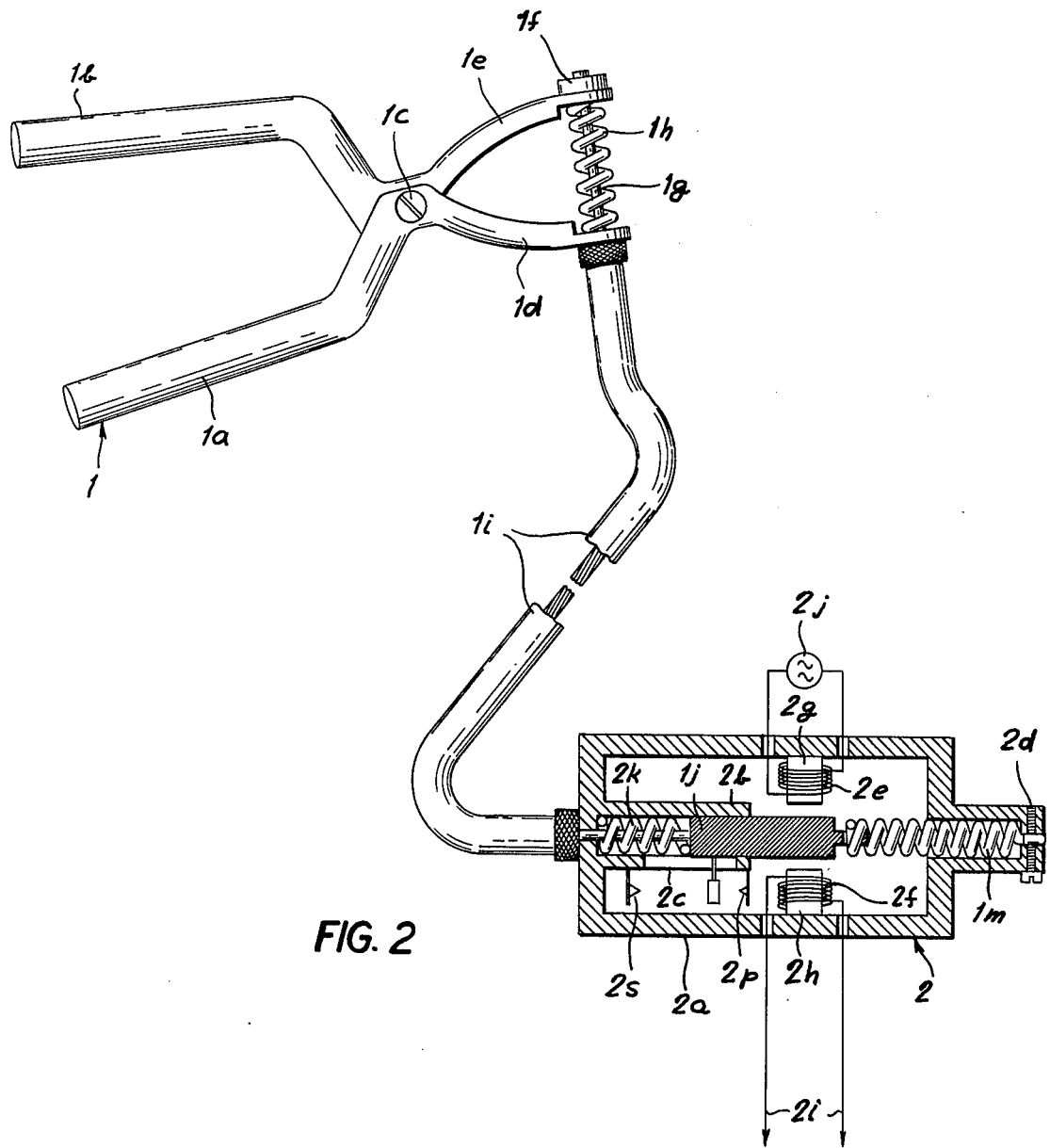
FIG. 2 is a perspective view, partly broken away and partly in diagrammatic form, of the actuator and transducer for producing the input signals to the circuit of FIG. 1.

The electrodynamograph according to the invention makes use of the device shown in FIG. 2 for measuring the exertions of the subject.

The hand-driven actuator 1 comprises a pair of levers 1a, 1b hinged to 1c and similar to the clutch levers of a motorcycle. The arms 1e and 1d of the levers 1a and 1b are coupled respectively to the Bowden core 1g via a nut 1f and a sheath 1i of a bowden cable running to the transducer 2. A coil spring 1h resists movement of the levers 1a and 1b together. The core of the Bowden cable is connected within the housing 2a of the transducer 2 to a movable metallic screen 1j centered between a pair of springs 1k and 1m and guided at 2b and 2c within the housing. When the handles 1a and 1b are released, the springs 1k and 1m return the handles and the plate 1j to their initial positions. The screen 1j is disposed between a pair of coils 2e and 2f anchored in the housing 2 and having iron cores 2g and 2h. When the screen 1j is fully withdrawn, the coils are inductively coupled and an output is generated in coil 2f and is detected at the terminals 2i. An audio frequency signal is applied as represented at 2j to the primary coil 2e. When the screen 1j is in place between the cores 2g and 2h, no output is obtained.

The transducer 2 is provided with a first set of contacts 2p which are closed upon initial movement of member 2j and another set of contacts 2s which are closed at the end of the stroke of member 2j, the contacts 2p and 2s being connected to the counters 9 and 10, respectively for registering the movements of the screen 1j thereon.

The subject who is to be tested squeezes with one hand the device 1 to transmit the force linearly through the cable to the movable screen 1j. The tested subject repeats the squeezing release operations, with maximum amplitude, until he no longer is able to continue the effort. Generally the test period is between 1 minute and 2 minutes. The squeezings are carried out in the rhythm or candence of the sound signals produced by the audio frequency generator at a rate determined by the switching rate of the multivibrator 6 and transmitted through the loudspeaker 7. The interruption frequency of the signals and the amplitude are both adjustable. The interruption takes place in the loudspeaker circuit and is achieved by the contacts of a relay controlled by the multivibrator and contained within the block 6.

As noted, the audio frequency current obtained at the output terminals of the audio frequency amplifier 4 also supplies the primary coil of the inductive transducer 2. When the screen is completely inserted between the coils, no current is found in the secondary winding. As the screen is withdrawn from between the coils, an audio frequency current is induced in the secondary winding of the transducer, the induced voltage being proportional to the linear shift of the screen. In the position in which the levers are not squeezed, the iron screen is entirely introduced between the coils of the transducer 2. When the levers are completely squeezed, the screen is withdrawn entirely from between the coils.

The audio frequency alternating current induced in the secondary winding of the transducer is shaped, filtered and amplified if desired and applied to the magnetoelectric instrument of the graphic paper tape recorder 8, e.g. through the contacts of a relay, periodically interrupted by the variable-frequency free-running multivibrator 5 which provides a time marking. As with the cadence of the acoustic signal, and the volume thereof, the frequency of the multivibrator producing the time markings can be adjustable from a control panel of the device. The periodic brief interruption of the signal applied to the pen of the recorder causes the pen to return periodically to its rest position, tracing a straight line.

These lines, automatically traced at regular distances and spacings at a rate which can be adjusted from a control panel of the instrument, constitute time markings. Between one marking line and the following line the interval can range from 3 to 30 seconds. Because of this time-marking facility it is possible to obtain on the same paper tape two different records with a single inscribing pen. One represents the effort curve and the other represents the effort as a function of time. The paper tape for the graphic recorder may be pre-marked and the latter driven at a given rate to provide time marking if desired.

The pairs of electrical contacts 2p and 2s for blocks 9 and 10 are alternatively closed when the transducer begins its motion and terminates its motion. Thus at the slightest squeezing of the levers of the hand-driven device 1, the counter 9 is triggered to register an operation. When the entire stroke of the levers is performed, the counter 2 is triggered. Concurrently with the operation of the counter 9, a signal light on a control panel (not shown) can be extinguished to indicate that the device is functioning properly and has been properly connected to the electrical supply network. The light also shows the state of the movements of the subject acting upon the hand-driven device.

The registers of the counters 9 and 10 serve to indicate if, during the tests, the subject has or has not utilized the entire stroke of the hand-driven device 1. If the numerical values registered by the counters 9 and 10 are equal or close to equal, it follows that the test was carried out with full stroke for each stroke. If there is a large disparity between the counters, it indicates that in many cycles of operation a full stroke was not applied.

The device thus traces a curve on the paper tape of recorder 8 which represents the movements of the hand-driven device. If desired, the trace can represent a mean or integrated value of such movements. If an integrated value is desired, a switch on the control panel may be operated to connect a condenser of suitable capacitance in parallel with the recorder.

The system is supplied with a double-stabilized power until 11 as noted above. This unit can include a ferro-resonant stabilizer and an electronic stabilizer with Zener diode and transistor control. The result of this dual stabilization is that the electrodynamograph can be connected to networks of 220 V or 120 V without switching over and without causing voltage variations at the various terminals of the circuit elements. Damage to the electrodynamograph by erroneous network connection can be avoided together with the perturbations of voltage fluctuations in the mains or network.

Before any physical or intellectual activity the subject is caused to operate with one hand at an established rhythm, determined by the acoustic output of the loudspeaker, the hand-driven device 1 until the flexor muscles of the hand become tired and the subject cannot continue the operations. There is thus obtained a first curve on the tape. After completion of the physical or intellectual activity, the subject repeats the test to produce a second curve on the tape which is of a different configuration. The two curves are measured with a planimeter to produce a numerical output representing the integral under each curve and the area thereof.

The two numerical values N and N' are combined in accordance with the relationship (N−N'/N) × 100 to give a percentage value representing the change in available muscular activity brought about by the physical or intellectual work.

The electrodynamograph according to the invention has the following important advantages:

Firstly it can be transistorized and is easily transportable.

Secondly, it enables the muscular effort to be transformed into a percent value in an objective, accurate and reproducible way.

Thirdly, it makes it possible to obtain graphic records of each subject separately and enables the condition of the subject generally to be monitored as a function of time.

Further, it enables the work capacity and tenacity of the subject to be ascertained, permits the technique to be used for professional selection and application of the tests in an educational manner, and enables verification of the consequences of ergonomic work.

Finally, it enables the effectiveness of medical treatment as a function of time to be ascertained and allows the testing of athletic performance.

We claim:
1. An electrodynamograph comprising:
a hand-driven device repeatedly squeezable and provided with a transducer;
a recorder operatively connected to said transducer for producing a trace of the output thereof as a function of time;
an audio-frequency generator producing an acoustic signal;
a multivibrator control switch connected to said audio-frequency generator for interrupting the signal produced thereby;
a loudspeaker connected to said multivibrator control switch for rendering the audio-frequency output audible to the test subject at a predetermined cadence, said cadence and the amplitude of the audio output of said multivibrator control switch being adjustable, said transducer comprising a primary coil and a secondary coil inductively coupled to said primary coil, and a metallic screen displaceable between said coils by said device, said audio-frequency generator applying said audio frequency signal to said primary coil to generate an audio-frequency current in said secondary coil;
a multivibrator switch of adjustable frequency connected between said transducer and said recorder for periodically interrupting the signal applied to said recorder to provide time markings on said trace; and
a first counter registering stroke-start operations of said device and a second counter registering stroke end operations of said device, said counters being controlled by two pairs of electrical contacts associated with said transducer whereby a first of said contacts is closed at the beginning of said stroke and the second of said contacts at the end of said stroke.

2. The electrodynamograph defined in claim 1, further comprising a condenser connected in parallel to said recorder for registering as a trace an integrator signal derived from said transducer.

3. The electrodynamograph defined in claim 1, further comprising a Bowden cable connecting said device with said transducer.

* * * * *